(12) United States Patent
Farmer et al.

(10) Patent No.: US 8,409,524 B2
(45) Date of Patent: *Apr. 2, 2013

(54) AERIAL VEHICLE WITH PAINT FOR DETECTION OF RADIOLOGICAL AND CHEMICAL WARFARE AGENTS

(75) Inventors: Joseph C. Farmer, Tracy, CA (US); James L. Brunk, Martinez, CA (US); S. Daniel Day, Danville, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/365,144

(22) Filed: Feb. 2, 2012

(65) Prior Publication Data

US 2012/0135528 A1 May 31, 2012

Related U.S. Application Data

(62) Division of application No. 12/837,732, filed on Jul. 16, 2010, now Pat. No. 8,143,063, which is a division of application No. 11/293,657, filed on Dec. 1, 2005, now Pat. No. 7,780,912.

(60) Provisional application No. 60/712,006, filed on Aug. 26, 2005.

(51) Int. Cl.
*G01N 21/71* (2006.01)
*G01N 21/84* (2006.01)
*G01N 31/22* (2006.01)
*G01N 23/221* (2006.01)
*G01N 33/00* (2006.01)

(52) U.S. Cl. ............. 422/403; 422/82.05; 422/82.08; 422/400; 422/402; 422/425; 436/57; 436/58; 436/103; 436/104; 436/166; 436/172

(58) Field of Classification Search .... 422/82.05–82.08, 422/400, 402–403, 425; 436/2–3, 6, 103–104, 436/166, 169, 172, 57–58
See application file for complete search history.

(56) References Cited

U.S. PATENT DOCUMENTS

| | | | | |
|---|---|---|---|---|
| 2,918,033 A | * | 12/1959 | Snyder | 116/206 |
| 3,266,920 A | * | 8/1966 | Griffith | 106/413 |
| 3,287,156 A | * | 11/1966 | Griffith | 220/62.11 |
| 3,577,161 A | * | 5/1971 | Oberhoffer et al. | 250/484.3 |
| 3,657,538 A | * | 4/1972 | Fergason et al. | 250/473.1 |
| 3,769,510 A | * | 10/1973 | Kotera et al. | 250/459.1 |
| 3,927,328 A | * | 12/1975 | Kawabata et al. | 250/473.1 |
| 4,127,499 A | * | 11/1978 | Chen et al. | 252/301.17 |
| 4,240,992 A | * | 12/1980 | Petrie et al. | 264/21 |
| 4,411,989 A | * | 10/1983 | Grow | 435/20 |
| 4,650,329 A | * | 3/1987 | Barrett et al. | 356/481 |
| 4,742,227 A | * | 5/1988 | Takenaka | 250/336.1 |
| 4,788,126 A | * | 11/1988 | Feldman et al. | 430/138 |
| 4,876,058 A | * | 10/1989 | Fero et al. | 376/247 |
| 4,893,017 A | * | 1/1990 | Kronenberg | 250/370.07 |

(Continued)

OTHER PUBLICATIONS

Van Houten, K. A. et al, Journal of the American Chemical Society 1998, 120,12359-12360.*

(Continued)

*Primary Examiner* — Arlen Soderquist
(74) *Attorney, Agent, or Firm* — Eddie E. Scott

(57) ABSTRACT

A paint that warns of radiological or chemical substances comprising a paint operatively connected to the surface, an indicator material carried by the paint that provides an indication of the radiological or chemical substances, and a thermo-activation material carried by the paint. In one embodiment, a method of warning of radiological or chemical substances comprising the steps of painting a surface with an indicator material, and monitoring the surface for indications of the radiological or chemical substances. In another embodiment, a paint is operatively connected to a vehicle and an indicator material is carried by the paint that provides an indication of the radiological or chemical substances.

6 Claims, 3 Drawing Sheets

U.S. PATENT DOCUMENTS

| | | | | |
|---|---|---|---|---|
| 4,983,834 | A * | 1/1991 | Lindmayer et al. | 250/581 |
| 5,019,518 | A * | 5/1991 | Diehl et al. | 436/172 |
| 5,032,380 | A * | 7/1991 | Novak et al. | 436/120 |
| 5,065,031 | A * | 11/1991 | Moscovitch | 250/486.1 |
| 5,084,623 | A * | 1/1992 | Lewis et al. | 250/474.1 |
| 5,179,281 | A * | 1/1993 | Tawil et al. | 250/337 |
| 5,206,118 | A * | 4/1993 | Sidney et al. | 430/343 |
| 5,322,797 | A * | 6/1994 | Mallow et al. | 436/106 |
| 5,332,548 | A * | 7/1994 | Moore | 422/421 |
| 5,447,688 | A * | 9/1995 | Moore | 422/424 |
| 5,451,792 | A * | 9/1995 | Maguire et al. | 250/474.1 |
| 5,651,804 | A * | 7/1997 | Debnath | 65/30.13 |
| 5,656,815 | A * | 8/1997 | Justus et al. | 250/337 |
| 5,935,862 | A * | 8/1999 | Novak | 436/104 |
| 5,976,881 | A * | 11/1999 | Klingner | 436/3 |
| 6,127,685 | A * | 10/2000 | Yoder et al. | 250/472.1 |
| 6,198,108 | B1 * | 3/2001 | Schweitzer et al. | 250/472.1 |
| 6,218,846 | B1 * | 4/2001 | Ludwig et al. | 324/713 |
| 6,276,214 | B1 * | 8/2001 | Kimura et al. | 73/795 |
| 6,300,638 | B1 * | 10/2001 | Groger et al. | 250/458.1 |
| 6,316,782 | B1 * | 11/2001 | Akselrod et al. | 250/582 |
| 6,376,845 | B1 * | 4/2002 | Purtle | 250/491.1 |
| 6,403,329 | B1 * | 6/2002 | Novak et al. | 435/20 |
| 6,406,914 | B1 * | 6/2002 | Kaburaki et al. | 436/1 |
| 6,414,324 | B1 * | 7/2002 | Colyott et al. | 250/484.5 |
| 6,484,660 | B1 * | 11/2002 | English | 114/312 |
| 6,531,217 | B1 * | 3/2003 | Martin et al. | 428/364 |
| 6,627,891 | B1 * | 9/2003 | Warner et al. | 250/337 |
| 6,644,917 | B2 * | 11/2003 | Zhao et al. | 415/200 |
| 6,750,458 | B1 * | 6/2004 | Rourk | 250/474.1 |
| 6,809,648 | B1 * | 10/2004 | Fleming | 340/601 |
| 6,909,098 | B2 * | 6/2005 | Bross et al. | 250/367 |
| 7,173,702 | B2 * | 2/2007 | Maurer et al. | 356/417 |
| 7,227,158 | B1 * | 6/2007 | Patel et al. | 250/484.5 |
| 7,319,039 | B2 * | 1/2008 | Sullivan | 436/172 |
| 7,330,128 | B1 * | 2/2008 | Lombardo et al. | 340/693.5 |
| 7,780,912 | B2 * | 8/2010 | Farmer et al. | 422/50 |
| 7,780,913 | B2 * | 8/2010 | Farmer | 422/50 |
| 8,133,735 | B2 * | 3/2012 | Farmer | 436/2 |
| 2003/0007089 | A1 * | 1/2003 | Rosiene et al. | 348/384.1 |
| 2003/0138345 | A1 * | 7/2003 | Schwabe | 422/22 |
| 2003/0193032 | A1 * | 10/2003 | Marshall | 250/474.1 |
| 2004/0035498 | A1 * | 2/2004 | Kinlen | 148/250 |
| 2004/0109853 | A1 * | 6/2004 | McDaniel | 424/94.6 |
| 2005/0089142 | A1 * | 4/2005 | Marek | 378/98.8 |
| 2005/0164169 | A1 * | 7/2005 | Malak | 435/5 |
| 2005/0208290 | A1 * | 9/2005 | Patel | 428/323 |
| 2006/0011776 | A1 * | 1/2006 | Maurer et al. | 244/1 R |
| 2006/0145091 | A1 * | 7/2006 | Patel | 250/474.1 |
| 2008/0165344 | A1 * | 7/2008 | Treado et al. | 356/72 |
| 2009/0001286 | A1 * | 1/2009 | Kearfott | 250/484.2 |

OTHER PUBLICATIONS

Jenkins, A. L. et al, Analytical Chemistry 1999, 71, 373-378.*
Russell, R. J. et al, Analytical Chemistry 1999, 71, 4909-4912.*
Huston, A. L. et al, Nuclear Instruments and Methods in Physics Research B 2001, 184, 55-67.*
Levitsky, I. A. et al, Journal of Physical Chemistry B 2001, 105, 8468-8473.*
Kowatari, M. et al, Nuclear Instruments and Methods in Physics Research A 2002, 480, 431-439.*
Zhang, S.-W. et al, Journal of the American Chemical Society 2003, 125, 3420-3421.*
Khalil, G. E. et al, Sensors and Actuators B 2004, 97, 13-21.*
Agarwala, V. S., "Corrosion 'Health' Monitoring Systems for Reduced Maintenance/Repair and Increased System Reliability," Proc. Int. Conf. on Corrosion CONCORN (1997) pp. 140-150.*
Davis, G. D.,et al., "Corrosion Protection and Condition Monitoring Using 'Smart' Appliques," Coatings & Linings, Materials Performance, 2004, pp. 32-36.*
Zhang, Y,, "Intelligent Coating for Nondestructive Structural Condition Monitoring," Sensors/Smart Materials, (2004) pp. 365-373.*
Otto, J., et al., "Detection of Hidden Corrosion Under Paint," Nondestructive i Characterization of Materials XI, Proceedings of the Int'l Syrup. 11th, con't Berlin, Germany (2002) pp. 297-307.*
de Ment, J., Journal of Chemical Education 1944, 21, 116-125 and 154.*
Jenkins, R. et al, X-Ray Spectrometry 1975, 4, 33-42.*
Pressyanov, D, S, et al, Environment International 1996, 22, Supplement 1, 5491-5493.*

* cited by examiner

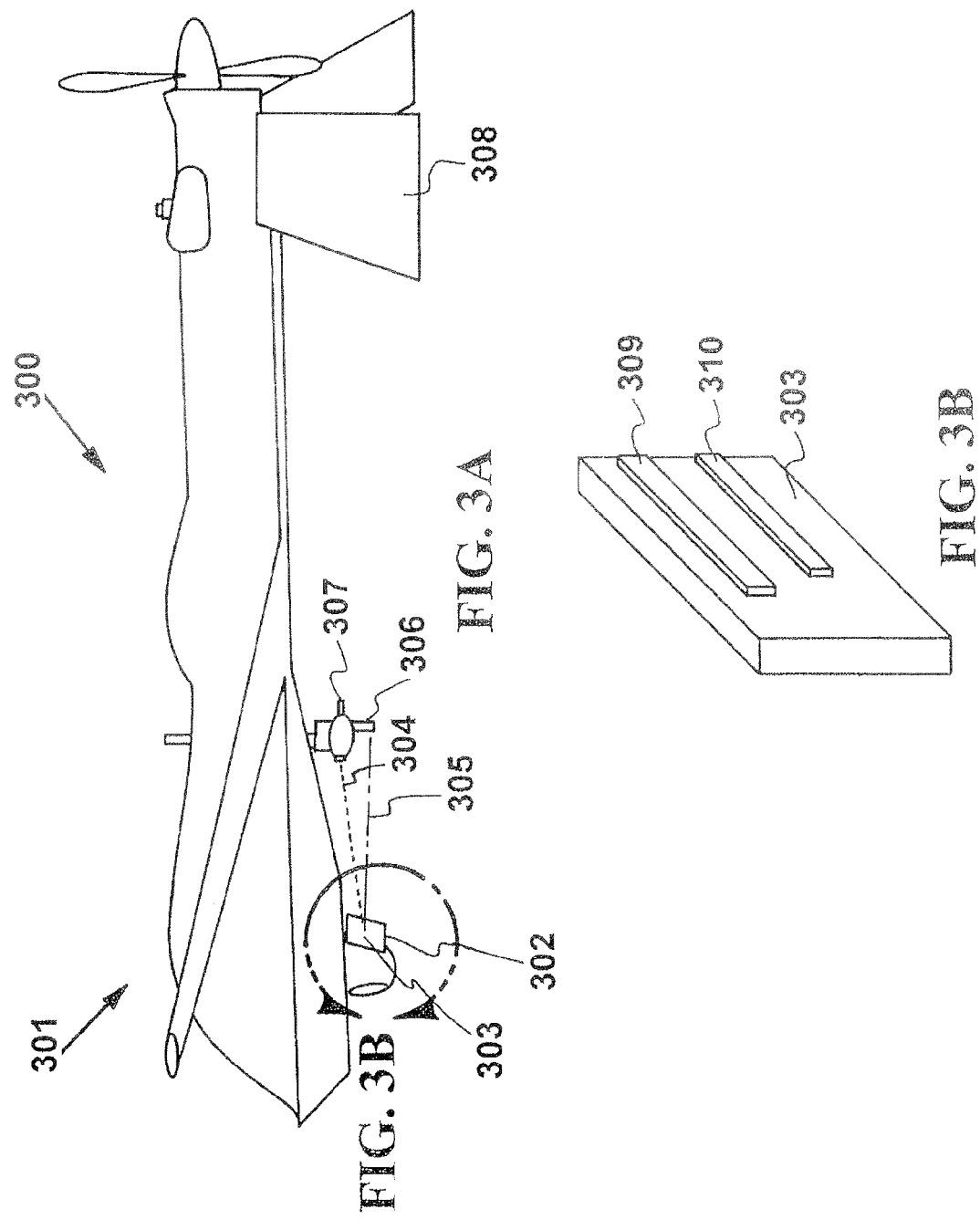

AERIAL VEHICLE WITH PAINT FOR DETECTION OF RADIOLOGICAL AND CHEMICAL WARFARE AGENTS

CROSS-REFERENCE TO RELATED APPLICATIONS

This application is a Divisional of U.S. application Ser. No. 12/837,732, filed Jul. 16, 2010, now U.S. Pat. No. 8,143,063, which is a US divisional application of U.S. application Ser. No. 11/293,657, filed Dec. 1, 2005, now U.S. Pat. No. 7,780,912, which claims the benefit of U.S. Provisional Patent Application No. 60/712,006 filed Aug. 26, 2005, all of which are incorporated herein by reference.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to detection and more particularly to paint for detection of radiological and chemical materials.

2. State of Technology

Paints/coatings of the present invention enable the detection of radiological and chemical warfare agents through direct or instrument-assisted visual inspection. Such paints and coatings can warn soldiers of radiological and chemical attack. This feature can be added to tactical vehicles during maintenance operations. The use of paints inside buildings, trains, and subway tunnels would provide a means of detecting the presence of radiological and chemical warfare agents over large surfaces.

Radiological warfare agents include radiological bombs, dirty bombs, and other systems for releasing radioactive material. Current concerns about radiological warfare tend to be focused on bombs and on deliberate pollution of air, water, or ground. Some radiological agents, such as plutonium, are extremely virulent, and can kill over time with near-certainty at doses as low as one microgram. However, being an extremely heavy metal, and extremely dangerous and difficult to grind to powder, it seems unlikely that it would be an effective means of such warfare. It is more likely that lighter elements might be used, those isotopes that are very unstable and may be created just in time for use. It is therefore believed that the existing regimes of inspection of labs and other facilities handling radioactive material, if strictly enforced, can effectively prevent their use to kill in a systematic and deliberate manner. For these reasons, some experts consider radiological warfare to have the same problems as chemical warfare agents.

Nerve agents are potent cholinesterase-inhibiting organophosphourous compounds. Symptoms of muscarinic and nicotinic overstimulation include abdominal pain, vomiting, diarrhea, excessive salivation and sweating, bronchospasm, copious pulmonary secretions, muscle fasciculations and weakness, and respiratory arrest. Seizures, bradycardia, or tachy-cardia may be present. Severe dehydration can result from volume loss due to sweating, vomiting, and diarrhea. Sequelae can include polyneuropathy and neuropsychiatric changes.

U.S. Pat. No. 5,935,862 to Thaddeus J. Novak issued Aug. 10, 1999 for microspot test methods and a field test kit for on-site inspections of chemical agents provides the following state of technology information: "Over the years, various highly toxic chemical warfare agents (CWA's) have been developed and stockpiled by several nations. In view of the biological hazards associated with CWA's and degradation products thereof, chemical warfare conventions (CWC's) have been developed by certain countries. These CWC's monitor, identify and, if necessary, dispose of CWA's which are not in compliance with the convention. As a result of the convention, it is often necessary to conduct inspections of various sites in order to assure compliance.... In view of the advantages of rapidly and accurately identifying the presence of CWA's and associated by-products, and further in view of the need to address the shortcomings associated with currently available detection methods, there is still a need for new and improved detection methods and kits."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a paint that warns of radiological or chemical substances comprising a paint operatively connected to the surface, an indicator material carried by the paint that provides an indication of the radiological or chemical substances, and a thermo-activation material carried by the paint. In one embodiment the present invention provides a method of warning of radiological or chemical substances comprising the steps of painting a surface with an indicator material, and monitoring the surface for indications of the radiological or chemical substances. In another embodiment the present invention provides a system that warns of radiological or chemical substances comprising a vehicle, a paint operatively connected to the vehicle, an indicator material carried by the paint that provides an indication of the radiological or chemical substances, and a thermo-activation material carried by the paint.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 3 illustrates yet another embodiment of a system of the present invention.

DETAILED DESCRIPTION OF THE INVENTION

Figure 1:
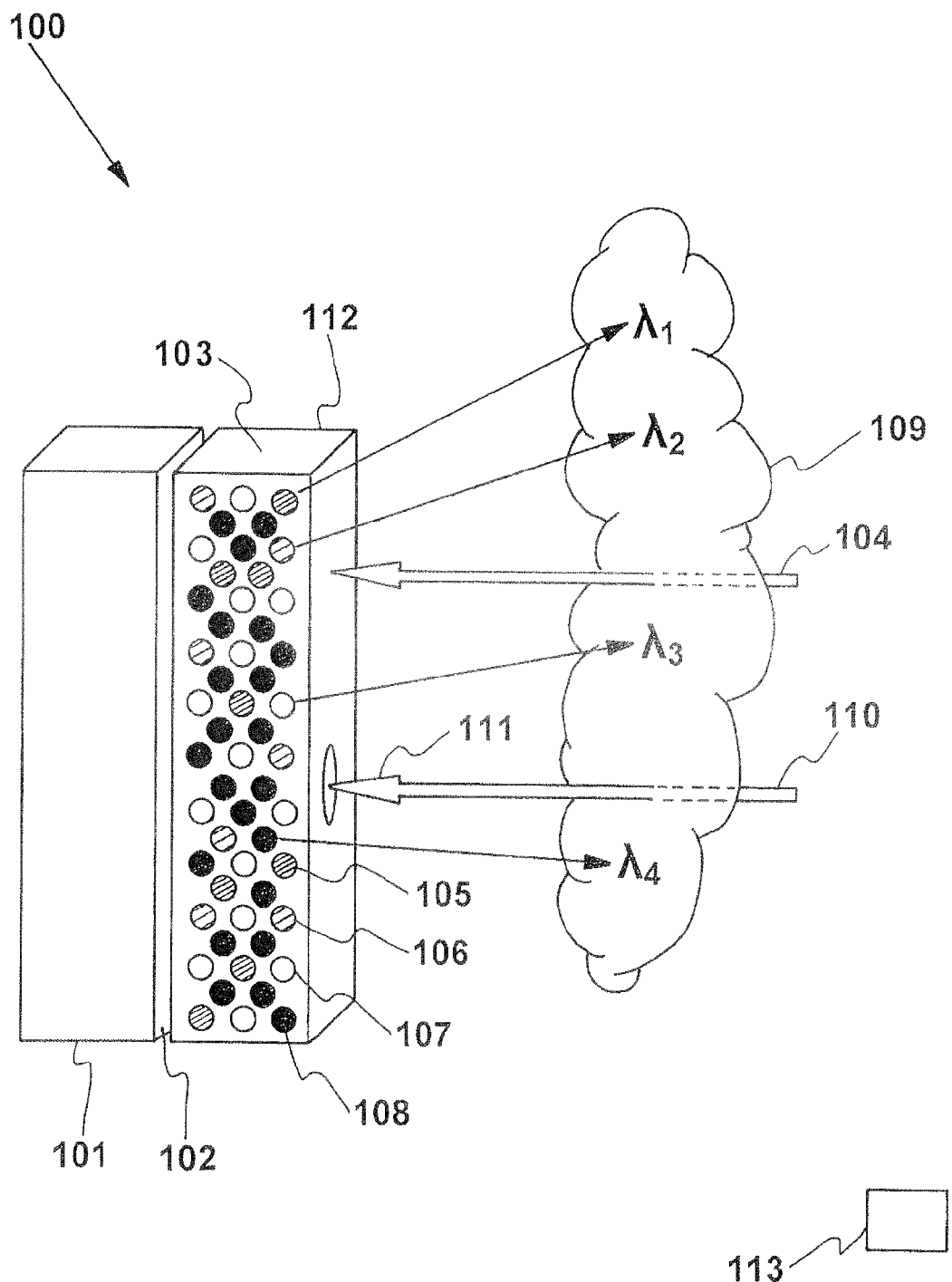
FIG. 1 illustrates a system that provides a warning of radiological warfare agents.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring to the drawings embodiments of systems of the present invention are illustrated. The systems provide warning of radiological and chemical warfare agents. The systems comprise painting a surface of a relevant structure with indicator paint and monitoring the paint for indications of the radiological or chemical warfare agents. The paint 103 contains material that causes the paint to provide an indication of the chemical or radiological warfare agents.

Radiological Warfare Agents (RWAs) are detected through scintillation. Special crystalline pigments are added to the paint that produce luminescence when irradiated by alpha, beta, or gamma rays. The luminescence is used to stimulate florescence in dyes within the polymeric binder of the paint.

In Chemical Warfare Agents (CWA) detection, an alkyloxy methylphosphonic acid in the paint is reacted with an appropriate dehydrating agent to produce cholinesterase inhibitor. The cholinesterase inhibitor is then detected with a pH-sensitive, chromogenic indicator molecule.

Referring to the drawings and in particular to FIG. 1, an embodiment of a system of the present invention is illustrated. This embodiment is designated generally by the reference numeral 100. The system 100 provides a warning of radiological warfare agents. The system 100 for warning of radiological warfare agents comprises painting a surface 102 of a relevant structure 101 with an indicator paint 103 and monitoring the paint 103 for indications of the radiological or chemical warfare agents. The Radiological Warfare Agents (RWA) are illustrated by the cloud 109 in FIG. 1. The RWA could also be from a source of radiation such as a nuclear weapon. Also the radiation could come from a source such as a nuclear reactor.

The paint 103 contains material that causes the paint to provide an indication of the RWA or other source of radiation. The radiation is detected through scintillation. Special crystalline pigments are added to the paint that produce luminescence when irradiated by alpha, beta, or gamma rays. The luminescence is then be used to stimulate florescence in dyes within the polymeric binder of the paint.

Referring again to FIG. 1, the detection of RWA or other radiation by the paint 103 will be described in greater detail. The system 100 utilizes the inclusion of scintillation agents into the paint 103. Special pigments 105, 106, and 107, are added to the paint 103 that produce scintillation and luminescence $\lambda_1$, $\lambda_2$, and $\lambda_3$ when irradiated by alpha ($\alpha$), beta ($\beta$), and gamma ($\gamma$) rays 104. The pigments 105, 106, and 107 are contained in an optically transparent organic binder 112. Alpha scintillation pigments 105 produce the luminescence $\lambda_1$, Beta scintillation pigments 106 produce the luminescence $\lambda_2$. Gamma scintillation pigments 107 produce the luminescence $\lambda_3$. The scintillation is used to stimulate florescence thermal luminescent pigments 108 that are incorporated within the optically transparent organic binder 112 of the paint 103. The laser 110 directs a thermal pulse 111 onto the paint 103 that stimulates the scintillations.

These scintillations are detected by detector 113. For example, these scintillations can be detected directly with a photomultiplier tube (PMT) coupled with an amplifier and pulse-counting electronics, digital CCD-array cameras, or other such devices, or used to stimulate florescence in dyes within the polymeric binder 112 of the paint 103 with detection of the secondary emission. Some of the components that can be used in the system 100 are: (1) Inorganic Scintillators, such as LiI (Sn) for neutron detection, ZnS (Ag) for $\alpha$ detection, NaI (Tl) for $\gamma$ detection, CsI (Tl) for $\gamma$ detection, CsI (Na) for $\gamma$ detection, BGO for $\gamma$ detection, and $BaF_2$ for $\gamma$ detection; and (2) Organic Scintillators, such as anthracene for $\beta$ and neutron detection, trans-stilbene for detection, p-terphenyl for $\beta$ detection, diphenylorazole for $\beta$ and neutron detection, tetraphenyl butadiene for $\beta$ detection, and terphenyl in polystyrene for $\beta$ detection. These are incorporated into the paint 103, thereby imparting radiation sensitivity. It is to be understood that other active agents can also be used.

Applicant has successfully demonstrated radiation-sensitive paints of the present invention illustrated in FIG. 1. This has been accomplished with the successful detection of scintillations from painted surfaces irradiated by both alpha particles and gamma rays. Alpha particles from a weak 1-nCi plutonium-239 source were detected with a special scintillation paint formulation, a photomultiplier tube (PMT), and an appropriate pulse counting network. Parametric studies were performed, determining the scintillation rate as a function of coating thickness, and distance of separation between the coating and source. An optimum paint thickness was identified for this scenario. It was found that the paint has to be thick enough to provide an easily detectable level of scintillation, but not so thick that the scintillations undergo self-absorption by the paint before reaching the detector. Gamma rays from a 100-µCi radium-226 source were also detected with another special scintillation paint formulation, by performing time-lapse photography with a commercially available 12.8-megapixel camera.

The paint illustrated by the system 100 illustrated in FIG. 1 can be applied using various application techniques. For example, numerous methodologies can be used for the production of derivative-type paints and coatings for detecting the presence of radiological agents on or near surfaces, and for the production of "integrating" paints and coatings for quantifying long-term exposure to doses of radiation. These coatings incorporate scintillation and/or thermo-luminescent materials as pigments and can be easily produced with a variety of processes including, organic polymeric binders, spray-on paints or coatings with organic polymeric binders, brush-on paints or coatings with organic polymeric binders, coatings and films produced with web coater and organic polymeric binders, powder coatings, inorganic ceramic/metallic binders, cold-spray processes, and thermal-spray processes.

The paints and coatings can be interrogated by any one of numerous systems. These include, but are not limited: (1) instantaneous detection of alpha-, beta- or gamma-induced scintillations from pigment particles with a PMT coupled to an amplifier and pulse-counting electronics, a digital CCD-array camera, or other such devices, for derivative-type coatings; or (2) laser-pulse, filament, or localized-microwave heating to induce photon emission from irradiated thermo-luminescent pigment particles, followed by detection with a PMT coupled to an amplifier and pulse-counting electronics, a digital CCD-array camera, or other such devices, for integral-type coatings, which integrate flux over the exposure time to provide a signal proportional to dose.

The present invention illustrated by the system 100 illustrated in FIG. 1 has may uses. For example radiation-sensitive paints and coatings can be used to monitor exposure in various scenarios of interest: (1) as paints for buildings and equipment in industrial plants involved in the production of nuclear and radiological materials; (2) as paints for the inside of nuclear power plants, nuclear powered ships, and submarines; (3) as paints for trucks and shipping containers and road-side facilities along shipping routes; (4) as paints for unmanned aerial vehicles, micro airships, and other surveillance devices; and (5) as paints for the detection and monitoring of activities involving radiological materials. In addition to enabling the long-term exposure (dose) of operating personnel in nuclear plants and nuclear-powered ships to be monitored, surfaces coated with these paints can be used to track and image the spread of radioactive contamination. Ultimately, thermo-luminescent paints and coatings could be used as a basis for qualifying the receipt of shipping containers for acceptance into the United States, where such qualification could be done through field interrogation of the painted surface, or through quantification of sampled paint chips.

Figure 2:
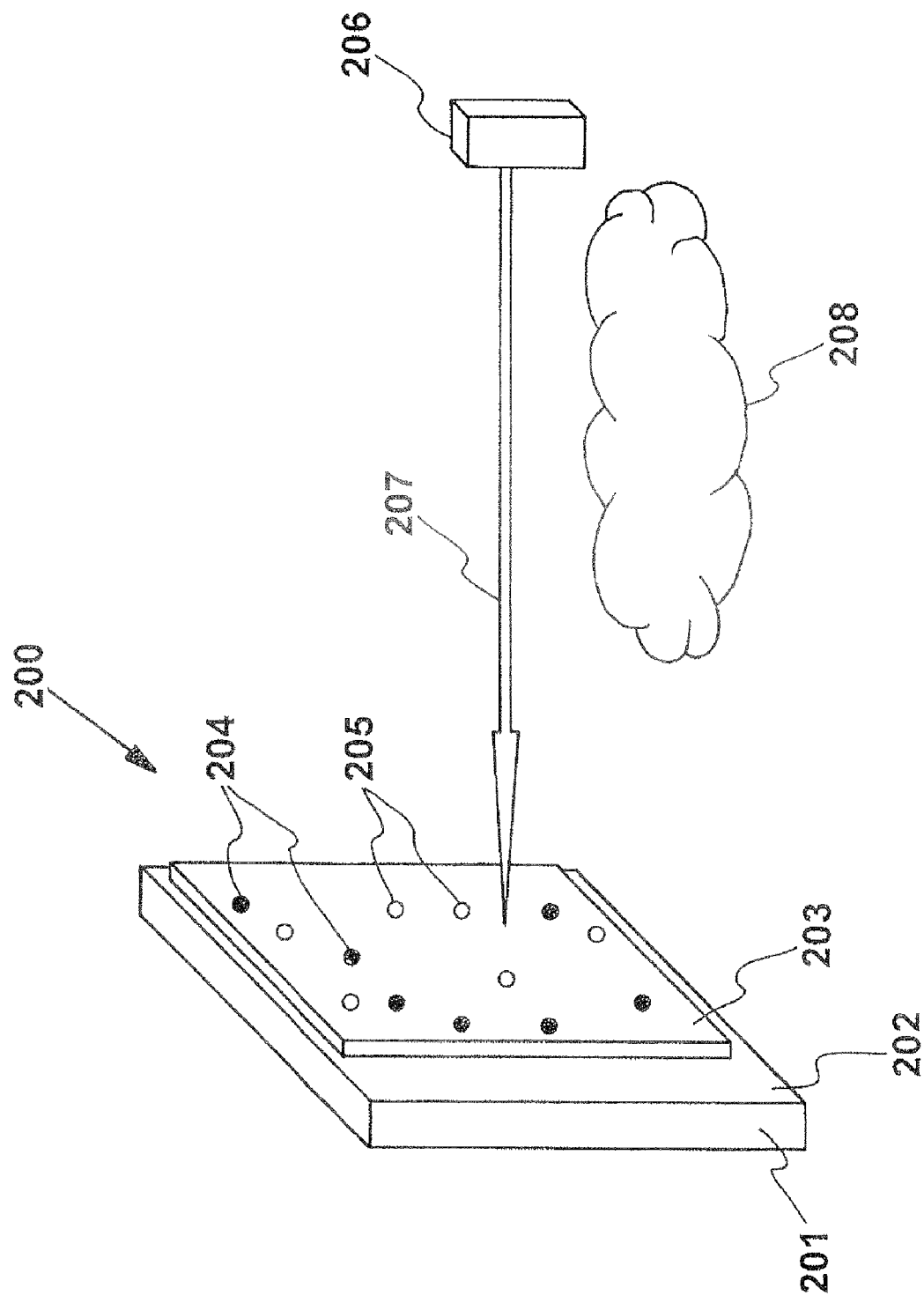
FIG. 2 illustrates another embodiment of a system of the present invention.

Referring now to FIG. 2, another embodiment of a system of the present invention is illustrated. This embodiment of the system is designated generally by the reference numeral 200. The system 200 provides a warning of chemical warfare agents. The Chemical Warfare Agents (CWA) are illustrated by the cloud 208. The system 200 for warning of chemical warfare agents comprises painting a surface 202 of a relevant structure 201 with an indicator paint 203 and monitoring the paint 203 for indications of the chemical warfare agents. The paint 203 contains material that causes the paint to provide an indication of the chemical warfare agents. In one embodiment of the system 200, Chemical Warfare Agents (CWA) detection, an alkyloxy methylphosphonic acid in the paint 204 is reacted with an appropriate dehydrating agent to produce cholinesterase inhibitor. The cholinesterase inhibitor is then detected with a pH-sensitive, chromogenic indicator molecule. In specific embodiments, the indicator paint 203 is further developed to enable dose recording due to any historic exposure to radiation. This second class of paint or coating, referred to here as an integrating paint or coating, depends upon thermal luminescence as a means of recording accumulated dose. In this case, an inorganic pigment (thermal luminescent material) produces luminescence proportional to radiation exposure (dose) during post-exposure heating.

Referring again to FIG. 2, the detection of Chemical Warfare Agents (CWA) by the paint 203 will be described in greater detail. For example the cloud 208 can include nerve agents that are potent cholinesterase-inhibiting organophosphourous compounds. Symptoms of muscarinic and nicotinic overstimulation include abdominal pain, vomiting, diarrhea, excessive salivation and sweating, bronchospasm, copious pulmonary secretions, muscle fasciculations and weakness, and respiratory arrest. Seizures, bradycardia, or tachy-cardia may be present. Severe dehydration can result from volume loss due to sweating, vomiting, and diarrhea. Sequelae can include polyneuropathy and neuropsychiatric changes.

The system 200 imparts chemical sensitivity to the paint or coating 203 to enable the detection of the CWA in the cloud 208. For example, U.S. Pat. No. 5,935,862 to Thaddeus J. Novak and U.S. Pat. No. 6,403,329 to Thaddeus J. Novak et al describe an alkyloxy methylphosphonic acid that is reacted with appropriate dehydrating agents to produce cholinesterase inhibitor. U.S. Pat. No. 5,935,862 and U.S. Pat. No. 6,403,329 are incorporated herein by reference. The indicator paint 203 is further developed to enable dose recording due to any historic exposure to radiation. This second class of paint or coating, referred to here as an integrating paint or coating, depends upon thermal luminescence as a means of recording accumulated dose. In this case, an inorganic pigment (thermal luminescent material) produces luminescence proportional to radiation exposure (dose) during postexposure heating.

Some of the reagents involved used in the system 200 are: (1) Methylphosphonic Acid (MPA) & Alkyloxy Methylphosphonic Acids (AMPA), ethyl MPA (EMPA), isopropyl MPA (IMPA), cyclohexyl MPA (CMPA), pinacolyl MPA (PMPA), O-ethyl methylphosphonothioic acid (EMPTA), and 1,4-dithiane (DITHIANE); (2) Esterification Reagents, dialkyl sulfate, and dialkyl iodide; (3) Dehydrating & Other Reagents, 1,3-dicyclohexylcarbodiimide and 1,3-diisopropylcarbodiimide. (4) Chromogenic Detector Reagent, bromcresol green, 7,7,8,8-tetracyanoquinodimethane (TCNQ), and gold chloride with/without NaOH; and (5) Solid Absorbent, alumina and silica. The following specific examples are embodiments of the system 200: $CaSO_4(Tu)$, $Li_2B_4)7(Cu)$, and $Al_2O_3$.

The cholinesterase inhibitor, produced by reacting AMPA with an appropriate dehydrating agent, is then detected with a pH-sensitive, chromogenic indicator molecule. Bromcresol green is a common chromogenic indicator, which is blue at $pH \geq 5.4$, and yellow at $3.8 < pH < 5.4$. The presence of cholinesterase inhibitor at the surface of the solid absorbent material lowers the pH from above 5.4 to an acidic level between 3.8 and 5.4, thereby producing a color change.

The system 200 for detection of chemical warfare agents utilizes the incorporation of the esterification and dehydration reagents into the coating 205 in a way to maintain their activity. This includes direct incorporation the functionality into the polymeric coating, triggered release of the reagents from capsules, and transport-limited time-release.

The paints and coatings can be interrogated by any one of numerous systems. These include, but are not limited: (1) instantaneous detection of alpha-, beta- or gamma-induced scintillations from pigment particles with a PMT coupled to an amplifier and pulse-counting electronics, a digital CCD-array camera, or other such devices, for derivative-type coatings; or (2) laser-pulse, filament, or localized-microwave heating to induce photon emission from irradiated thermo-luminescent pigment particles, followed by detection with a PMT coupled to an amplifier and pulse-counting electronics, a digital CCD-array camera, or other such devices, for integral-type coatings, which integrate flux over the exposure time to provide a signal proportional to dose.

Referring again to the drawings and in particular to FIGS. 3A and 3B, another embodiment of a system of the present invention is illustrated. This embodiment of the system is designated generally by the reference numeral 300. The system 300 provides a warning of radiological or chemical warfare agents encountered by an unmanned aerial vehicle (UAV) 301. As previously described, the Radiological Warfare Agents (RWAs) are detected through scintillation. Special crystalline pigments are added to the paint that produce luminescence when irradiated by alpha, beta, or gamma rays. The luminescence can then be used to stimulate florescence in dyes within the polymeric binder of the paint. Also, as previously described, the Chemical Warfare Agents (CWA) are detected through use of an alkyloxy methylphosphonic acid in the paint that is reacted with an appropriate dehydrating agent to produce cholinesterase inhibitor. The cholinesterase inhibitor is then detected with a pH-sensitive, chromogenic indicator molecule.

The UAV 301 is equipped with a camera 306. The camera 306 is moveable and can train its line of sight 305 to various locations including numerous locations on the body of the UAV 301. As illustrated in FIG. 3A, the camera line of sight 305 is trained on a viewing surface 303 on the body of the UAV 301. The camera line of sight 305 can be trained on other portions of the body of the UAV 301. For example an alternate viewing surface 308 is shown on one of the rear stabilizers of the UAV 301.

The UAV 301 is also equipped with a laser 307. The laser 307 is moveable and can train its laser beam 304 to various locations including numerous locations on the body of the UAV 301. As illustrated in FIG. 3A, the laser beam 304 is directed onto the viewing surface 303 on the body of the UAV 301. The laser beam 304 can be trained on other portions of the body of the UAV 301. For example, the laser beam 304 can be trained on the alternate viewing surface 308 shown on one of the rear stabilizers of the UAV 301.

Referring now to FIG. 3B, the viewing surface 303 is shown in greater detail. The viewing surface 303 includes two paint strips 309 and 310.

The paint strip 309 is a paint strip for chemical detection and the paint strip 310 is a paint strip for radiation detection. The paint strip 308 for chemical detection contains material that causes the paint to provide an indication of the chemical warfare agents.

Paint for chemical detection has been described previously in connection with FIG. 2 and that description is incorporated in this description of the paint strip 309 of the system 300. The paint strip 310 for radiation detection contains material that causes the paint to provide an indication of the radiation warfare agents.

Paint for radiation detection has been described previously in connection with FIG. 1 and that description is incorporated in this description of the paint strip 310 of the system 300.

The two paint strips 309 and 310 are further developed to enable dose recording due to any historic exposure to radiation. This second class of paint or coating, referred to here as an integrating paint or coating, depends upon thermal luminescence as a means of recording accumulated dose. In this case, an inorganic pigment (thermal luminescent material) produces luminescence proportional to radiation exposure (dose) during post-exposure heating. The laser 307 provides the heating of the paint strips 309 and 310 through the laser beam 304.

By monitoring the viewing area 303 with the camera 306, it is possible to monitor whether the UAV 301 has encountered chemical warfare agents or radiation warfare agents. Since UAVs are routinely equipped with cameras and the cameras and the cameras are moveable to view various portions of the body of the UAV, the addition of the system 300 provides a warning of chemical or radiological warfare agents is a simple and cost effective system. The system 300 can be retrofitted to existing UAVs with a minimum of cost and time.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A system for warning of radiological warfare agents and chemical warfare agents, comprising:
   an unmanned aerial vehicle;
   a viewing surface on said unmanned aerial vehicle;
   a first paint strip on said viewing surface, said first paint strip including a first indicator material carried by said first paint strip that provides an indication of the radiological warfare agents, said first indicator material including a first thermal luminescent material carried by said first paint strip;
   a second paint strip on said viewing surface, said second paint strip including a second indicator material carried by said second paint strip that provides an indication of the chemical warfare agents, said second paint strip including a second thermal luminescent material carried by said second paint strip; and
   a laser on said unmanned aerial vehicle, said laser including a laser beam adapted to be directed onto said first paint strip and said second paint strip for heating said first thermal luminescent material and said second thermal luminescent material.

2. The system for warning of radiological warfare agents and chemical substances warfare agents of claim 1 further comprising a camera on said unmanned aerial vehicle, said camera having a line of sight adapted to be trained on said first paint strip and said second paint strip.

3. The system for warning of radiological warfare agents and chemical warfare agents of claim 2 further comprising a rear stabilizer on said unmanned aerial vehicle and a second viewing surface on said rear stabilizer.

4. The system for warning of radiological warfare agents and chemical warfare agents of claim 2 further comprising a rear stabilizer on said unmanned aerial vehicle and a second viewing surface on said rear stabilizer wherein said laser beam is adapted to be directed onto said second viewing surface on said rear stabilizer.

5. A system for warning of radiological warfare agents and chemical warfare agents, comprising:
   an unmanned aerial vehicle;
   a viewing surface on said unmanned aerial vehicle;
   a first paint strip on said viewing surface, said first paint strip including a first indicator material carried by said first paint strip that provides an indication of the radiological warfare agents, said first indicator material including a first thermal luminescent material carried by said first paint strip;
   a second paint strip on said viewing surface, said second paint strip including a second indicator material carried by said second paint strip that provides an indication of the chemical warfare agents, said second paint strip including a second thermal luminescent material carried by said second paint strip;
   a laser on said unmanned aerial vehicle, said laser including a laser beam adapted to be directed onto said first paint strip and said first indicator material carried by said first paint strip and said first thermal luminescent material carried by said first paint strip; and onto said second paint strip and said second indicator material carried by said second paint strip and said second thermal luminescent material carried by said second paint strip; and
   a camera on said unmanned aerial vehicle, said camera having a line of sight adapted to be trained on said first paint strip and said second paint strip.

6. The system for warning of radiological warfare agents and chemical warfare agents of claim 5 further comprising a rear stabilizer on said unmanned aerial vehicle and a second viewing surface on said rear stabilizer wherein said laser beam is adapted to be directed onto said second viewing surface on said rear stabilizer.

* * * * *